United States Patent [19]

Pearson et al.

[11] 4,304,921

[45] Dec. 8, 1981

[54] METHOD OF PREPARING β-HALO ESTERS FROM CYCLIC ACETALS

[75] Inventors: Donald E. Pearson; Sidhaghatta D. Venkataramu; James H. Cleveland, Jr., all of Nashville, Tenn.

[73] Assignee: Vanderbilt University, Nashville, Tenn.

[21] Appl. No.: 176,411

[22] Filed: Aug. 8, 1980

[51] Int. Cl.³ .................... C07C 69/74; C07C 69/78; C07C 69/82; C07C 69/34; C07C 69/52
[52] U.S. Cl. ........................................ 560/1; 560/87; 560/111; 560/197; 560/223; 560/266
[58] Field of Search ................. 560/87, 1, 111, 197, 560/223, 266

[56] References Cited

U.S. PATENT DOCUMENTS 3,988,369 10/1976 Pearson .................... 260/544 R

OTHER PUBLICATIONS

Pearson, et al, Synthesis, No. 9, 621–624 (1976).
Pearson, et al, Synth. Commun., vol. 9, 5–10 (1979).

*Primary Examiner*—Natalie Trousof
*Assistant Examiner*—Vera C. Clarke

[57] ABSTRACT

Beta-halo esters, such as β-haloalkyl benzoates or terephthalates, are prepared by halogenative cleavage of cyclic acetals using trimethyl phosphate (TMP) or borate to mediate the reaction. The β-halo esters, which are obtained in high yields, can be used to form polymers or plasticizers. Neuromuscular blocking agents such as succinylcholine and related compounds can also be prepared.

12 Claims, No Drawings

METHOD OF PREPARING β-HALO ESTERS FROM CYCLIC ACETALS

BACKGROUND AND PRIOR ART

The method of this invention relates to the halogenation of organic compounds using trialkyl phosphate or similar compound to mediate the reaction. This reaction system and certain products obtainable thereby are described in United States Pat. No. 3,988,369. See, also, Pearson et al, Synthesis, No. 9 (1976) 621–624; and Pearson et al, *Synth. Commun.* 9, 5–10 (1979). As described in U.S. Pat. No. 3,988,369, phosphorus pentoxide may be present during the halogenation reaction. None of the cited prior art references describe the halogenation of cyclic acetals or similar compounds.

SUMMARY OF INVENTION

This invention is based in part on the discovery that commercially important halo esters can be produced in high yields (viz. 80–90%) when cyclic acetals are halogenated in the presence of trimethyl phosphate and in the absence of phosphorus pentoxide. It is also been found that trimethyl borate can be substituted for the trimethyl phosphate while still obtaining good yields although somewhat lower than with trimethyl phosphate. The halogen used in the reaction is bromine or chlorine, and the cyclic acetals are typically dioxalanes which may contain one or more acetal groups. A preferred class of reactants is (1,4-phenylene)bis[dioxolane] which result in haloalkyl terephthalates.

β-halo esters prepared in accordance with the process of the present invention are useful as synthetic intermediates for preparing polymers and plasticizers. Specific compounds prepared in accordance with the present invention can be used for manufacturing neuromuscular blocking agents such as succinylcholine and related compounds. For example, preferred products can be used for preparing Dacron-type polymers, polycarbonate polymers, or epoxy polymers. See *Chem. Abst.*, 59, 2698b (1963); *Chem. Abst.*, 63, 5864d (1965); and, *Chem. Abst.*, 68, 60132h (1968). The preparation of plasticizers from halo esters of the kind prepared by the method of the present invention is described in *Chem. Abst.*, 53, 23087g (1959). Succinylcholine and related compounds which are useful as neuromuscular blocking agents can be prepared from haloalkyl terephthalates. Such compounds are known to have neuromuscular blocking properties. See Goth, *Medical Pharm.*, 138–139 (1976, Mosby Co., St. Louis, Mo.).

DETAILED DESCRIPTION

The cyclic acetal starting materials used in the method of the present invention are available commercially or can be readily prepared from published procedures. In general, the acetal reagent contains at least one acetal group represented by:

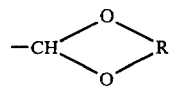

wherein R is a hydrocarbon group providing from 2 to 4 acetal ring carbons, which may be unsubstituted $CH_2$ groups or carbons in which one or both hydrogens have side chain substituents, such as an alkyl group of 1 to 3 carbons, or an aryl group such as phenyl. A preferred class of such acetal compounds can be represented by the formula:

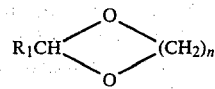

wherein "n" is a whole number from 2 to 4, indicating that the acetal ring may contain a total of from 5 to 7 members. The $R_1$ moiety which is bonded to the 2-carbon may comprise a wide variety of substituents, such as alkyl, alkylene, aryl, arylene, carbonyl, carbocyclic, etc. In a preferred subclass of compounds, $R_1$ is a phenylene group substituted with an acetal group of the same kind as previously described. The phenylene group may therefore have a symmetrical 1,4-acetal group substitution. The formula of such compounds is represented as follows:

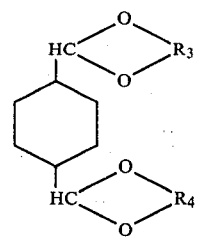

wherein $R_3$ and $R_4$ may be the same or different groups as described previously with respect to the R group of the first formula set out above or the $(CH_2)_n$ group of the second formula set out above.

The halogen reagent is preferably chlorine or bromine although other halogens such as iodine can be used. The halogen may be in the form $Br_2$, $Cl_2$, $BrCl$, or $ICl$, etc.

A mediating reagent must also be present in the reaction mixture. This is preferably trimethyl phosphate to obtain maximum yields, although trimethyl borate can also be used with satisfactory results.

In carrying out the reaction, the reaction conditions, proportions of reagents, and reaction procedures are the same as those previously described for the halogenation of organic compounds in the presence of trimethyl phosphate. See U.S. Pat. No. 3,988,369; Pearson, et al, Synthesis, No. 9, 621–624 (1976); and Pearson, et al, *Synth. Commun.*, 9, 5–10 (1979). In general, the acetal may be dissolved in the trimethyl phosphate (TMP) or trimethyl borate (TMB), and the halogen added as the reaction proceeds. An excess of the halogen will usually be employed, such as from 1 to 2 moles of halogen per mole of the acetal reactant. The TMP or TMB reagent will also usually be present in a large excess, and, in any event, should be present in a sufficient amount to react with the hydrogen halide by-product as formed. TMP or TMB hydrolyze in the presence of hydrogen halide, liberating methyl halide. Preferably, the TMP or TMB reagent will be used in a larger molar ratio than the halogen such as from about 1.2 to 50 moles of TMP or TMB per mole of halogen. The temperature of the reaction is not particularly critical, temperatures from 0° to 100° C. or higher being usable. Preferably, the reaction is carried out at a temperature of about 0° to 30° C.

Contrary to the teachings of U.S. Pat. No. 3,988,369, it is important to conduct the reaction in the absence of phosphorus pentoxide. Therefore, this reagent is not added and does not form in the course of the reaction. To prevent the halogen from reacting with the TMP or TMB, the reaction is preferably conducted in the dark. Light tends to catalyze the reaction of TMP or TMB with halogen. Also, to prevent undesirable side reactions, it is preferred to conduct the reaction in the absence of water and under a moisture-free atmosphere.

The halo ester products prepared by the method of this application can readily be recovered from the reaction mixture. For example, on completion of the reaction, water can be added with ice cooling. This will cause the separation of an oil layer, and/or the formation of a precipitate. The oil may be separated and extracted with a suitable solvent, such as hexane. Hexane does not dissolve TMP. If multiple extractions are employed, the organic solvent extracts are combined and washed with cold water. The extracts may be stirred with anhydrous $MgSO_4$ to remove water and to expel excess halogen. Thereafter, the organic solvent is evaporated, and the residue distilled under vacuum to obtain the final product. If desired this product may be redissolved in an organic solvent, and crystallized, or recrystallized to improve purity.

If a solid forms on dilution of the reaction mixture with water, this solid which may comprise only part of the product, may be washed with cold water, and recrystallized from an appropriate solvent. This product may be combined with the product extracted from the oil layer to provide the total product of the reaction. It will be appreciated, of course, that variations in these work-up procedures are within the skill of the art.

The method of this invention is further illustrated by the following examples:

EXAMPLES 1 TO 10

General Data

Melting points were determined with a Thomas-Hoover capillary melting point apparatus and are uncorrected. IR spectra were recorded on a Perkin-Elmer 727 infrared spectrophotometer. $1_H$ NMR spectra were obtained on a Jeol MH-100 nuclear magnetic resonance spectrometer. Elemental analyses were carried out by Galbraith Laboratories, Knoxville, Tenn. Trimethyl phosphate (TMP) was distilled over $P_2O_5$ (bp 52°–54° C. (0.5 mm)) and stored in amber-colored bottles.

Starting Materials

The starting acetals were prepared by boiling a mixture of the aldehyde (0.5 mol), glycol (0.55 mol), anhydrous benzene (100 mL), and a catalytic amount of p-toluenesulfonic acid with the removal of water (Dean-Stark). After evaporation of the solvent, the residue was distilled under vacuum. Melting and/or boiling points were determined.

General Procedure for the Preparation of Halohydrin Esters

The reactions were run at room temperature or at 0° C. as indicated in Table A. To a magnetically stirred solution or suspension of the acetal (0.1 mol) in 50 mL of TMP, protected from moisture and from the light, bromine (17.6 g, 0.11 mol in 50 mL of TMP) or chlorine (the gas was bubbled at 0° C. into 50 mL of TMP until 0.11 mol was absorbed) was added dropwise during 1 h. Bromine or chlorine do not react with TMP in the dark; Pearson, et al, Synthesis, 621 (1976). An exothermic reaction ensued in all the cases, and the temperature was not permitted to rise above 10° C. where the reaction was being run at 0° C. During the addition, a gas ($CH_3Br$ or $CH_3Cl$) was evolved. After being stirred for an additional period of time (Table A), about 300 mL of water was added with ice cooling. If an oil separated, it was extracted with hexane (3×50 mL), and the combined organic extract was washed with cold water (3×50 mL). After being stirred with anhydrous $MgSO_4$ in a hood to remove water and to expel excess bromine or chlorine, the solvent was removed in a rotoevaporator, and the residue was distilled under vacuum.

If a solid was formed on dilution with water, it was filtered, washed with cold water, and recrystallized from an appropriate solvent, as indicated in the footnote of Table A.

Physical data and yields are given in Table A.

If a comparable reaction is run without TMP, a mixture of two different halo esters is obtained. For example, 2-cyclohexyl-1,3-dioxolane was brominated in carbon tetrachloride by the following procedure;

Bromination Procedure

To a stirred solution of the acetal (15.62 g, 0.1 mol) in 50 mL of $CCl_4$ cooled to 0° C. was added bromine (17.6 g, 0.11 mol) dissolved in 50 mL of $CCl_4$ during 1 h ($CaCl_2$ tube). The temperature of the reaction was not allowed to rise above 8° C. by controlled addition. After the solution was stirred at room temperature for 3 h, the usual workup afforded a colorless oil (24.0 g). $^1H$ NMR analysis of the reaction product showed it to be a mixture of β-bromoethyl cyclohexane carboxylate, 2-(1-bromocyclohexane)-1,3-dioxalane, and β-bromoethyl-2-bromocyclohexanecarboxylate.

TABLE A

| Exp. No. | Cyclic Acetal Reaction | Halogen Reactant | Reaction Conditions[g] | Halo Ester Product | −bp(°C.) or mp (mm) | Yield[a] (%) |
|---|---|---|---|---|---|---|
| 1 | 2-phenyl-1,3-dioxolane | Br | RT/1h | β-bromoethyl benzoate | 100 (0.7) | 87 |
| 2 | 2-p-tolyl-1,3-dioxolane | Br | RT/1h | β-bromoethyl toluate | 95 (0.2) | 81 |
| 3 | 2-cylohexyl-1,3-dioxolane | Br | 0° C./1h RT/3h | β-bromoethyl cyclohexane carboxylate | 110 (5) | 88 |
| 4 | 5,5-dimethyl-2-phenyl-1,3-dioxane | Br | RT/2h | γ-bromo-β-β-dimethyl-propyl benzoate | 106–7 (0.4) | 80[b] |
| 5 | 2,2'-(1,4-phenylene)-bis [1,3-dioxolane] | Br | 0° C./2h | bis-β-bromoethyl terephthalate | 96–97[h] | 81[c] |
| 6 | 2,2'-(1,4-phenylene)-bis [1,3-dioxolane] | Cl | RT/2h | bis-β-chloroethyl terephthalate | 90–92[h] | 83[c] |
| 7 | 4-methyl-2-phenyl-1,3-dioxolane | Br | 0° C./1h | β-bromoisopropyl benzoate | 104 (0.8) | 93[e] |
| 8 | 4-methyl-2-phenyl-1,3-dioxolane | Cl | RT/1h | β-chloroisopropyl benzoate | 135 (1.1) | 88[e] |
| 9 | 2,2'-(1,4-phenylene) bis [4-methyl-1,3-dioxolane] | Br | RT/2h | bis-β-bromoisopropyl terephthalate | 48–50[h] | 72[b,c] |

TABLE A-continued

| Exp. No. | Cyclic Acetal Reaction | Halogen Reactant | Reaction Conditions[g] | Halo Ester Product | −bp(°C.) or mp (mm) | Yield[a] (%) |
|---|---|---|---|---|---|---|
| 10 | 2,2'-(1,4-phenylene) bis [4-methyl-1,3-dioxolane] | Cl | RT/2h | bis-β-chloroisopropyl terephtalate | 62–64[h] | 81[b,c] |

[a]Isolated yield of product after purification which was homogeneous by ¹H NMR.
[b]Satisfactory elemental analyses were obtained.
[c]Recrystallized from methanol-water.
[d]A mixture of cis and trans isomers (3:2).
[e]Contaminated with less than 5% of the regioisomer.
[f]Crystallized from an ether-hexane mixture.
[g]Room temperature (RT); hours (h).
[h]Melting point.

EXAMPLE 11

Trimethyl borate may be substituted for trimethyl phosphate for the halogenative cleavage of cyclic acetals by the method of this invention. In general, the yields of the halo esters are not as high. For example, bis-β-haloethyl terephthalate was prepared from 2,2'-(1,4-phenylene)bis[1,3-dioxolane] as follows:

To a magnetically stirred suspension of the diacetal (19.8 g, 0.1 mol) in 50 mL trimethylborate, cooled to 0° C., was added bromine (35.2 g, 0.22 mol) in 50 mL trimethylborate during 40 minutes. During the addition, the temperature was not permitted to rise above 10° C. The reaction mixture was allowed to warm to room temperature and stirring continued for 2 hours. After cooling in ice, cold water (300 mL) was added and the solid formed was filtered off, washed with cold water (2×50 mL) and air dried to give 75.2 g of the crude bromo compound, m.p. 75°–105° C.

The crude bromo compound was suspended in 500 mL methanol and magnetically stirred for 30 minutes and filtered. The weight of the solid was 1.0 g, m.p. 92°–93° C. The mother liquor was concentrated to about 300 mL and allowed to stand in the refrigerator. The solid was filtered. The weight of the solid was 6.1 g, m.p. 90°–91° C. The mother liquor was further concentrated to about 150 mL and diluted with water to turbidity, and allowed to stand in the refrigerator for one hour. The solid was filtered. The purified product weighed 20.0 g, m.p. 91°–92° C. The total yield was 22.1 g, giving a percent yield of 67%. The m.p. was 93°–94° C. (after drying).

We claim:

1. The method of preparing β-halo esters from cyclic acetals, comprising reacting under effective conditions for the reaction a cyclic acetal with halogen selected from the class consisting of bromine and chlorine in the presence of a reagent selected from the class consisting of trimethyl phosphate and trimethyl borate, in the absence of phosphorus pentoxide, said acetal containing at least one acetal group represented by:

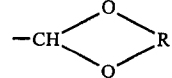

wherein R is a hydrocarbon group providing from 2 to 4 acetal ring carbons.

2. The method of claim 1 in which said reagent is trimethyl phosphate.

3. The method of claim 1 or claim 2 in which said cyclic acetal contains two of said acetal groups.

4. The method of claim 2 in which said cyclic acetal is a dioxolane.

5. The method of claim 2 in which said cyclic acetal is a (1,4-phenylene)bis[dioxolane] and the resulting halo ester is a haloalkyl terephthalate.

6. The method of claim 2 in which said cyclic acetal is a 2-phenyl-1,3-dioxolane and the resulting halo ester is β-haloethyl benzoate.

7. The method of claim 2 in which said cyclic acetal is a 2-p-tolyl-1,3-dioxolane and the resulting halo ester is β-haloethyl toluate.

8. The method of claim 2 in which said cyclic acetal is a 2-cylohexyl-1,3-dioxolane and the resulting halo ester is β-haloethyl cyclohexyl carboxylate.

9. The method of claim 2 in which said cyclic acetal is a 5,5-dimethyl-2-phenyl-1,3-dioxane and the resulting halo ester is a γ-halo-β,β-dimethylpropyl benzoate.

10. The method of claim 2 in which said cyclic acetal is a 2,2'-(1,4-phenylene)bis[1,3-dioxolane] and the resulting halo ester is a bis-β-haloethyl terephthalate.

11. The method of claim 2 in which said cyclic acetal is a 4-methyl-2-phenyl-1,3-dioxolane and the resulting halo ester is a β-haloisopropyl benzoate.

12. The method of claim 2 in which said cyclic acetal is 2,2'-(1,4-phenylene)bis[4-methyl-1,3-dioxolane] and the resulting halo ester is a bis-β-haloisopropyl terephthalate.

* * * * *